Figure 1:
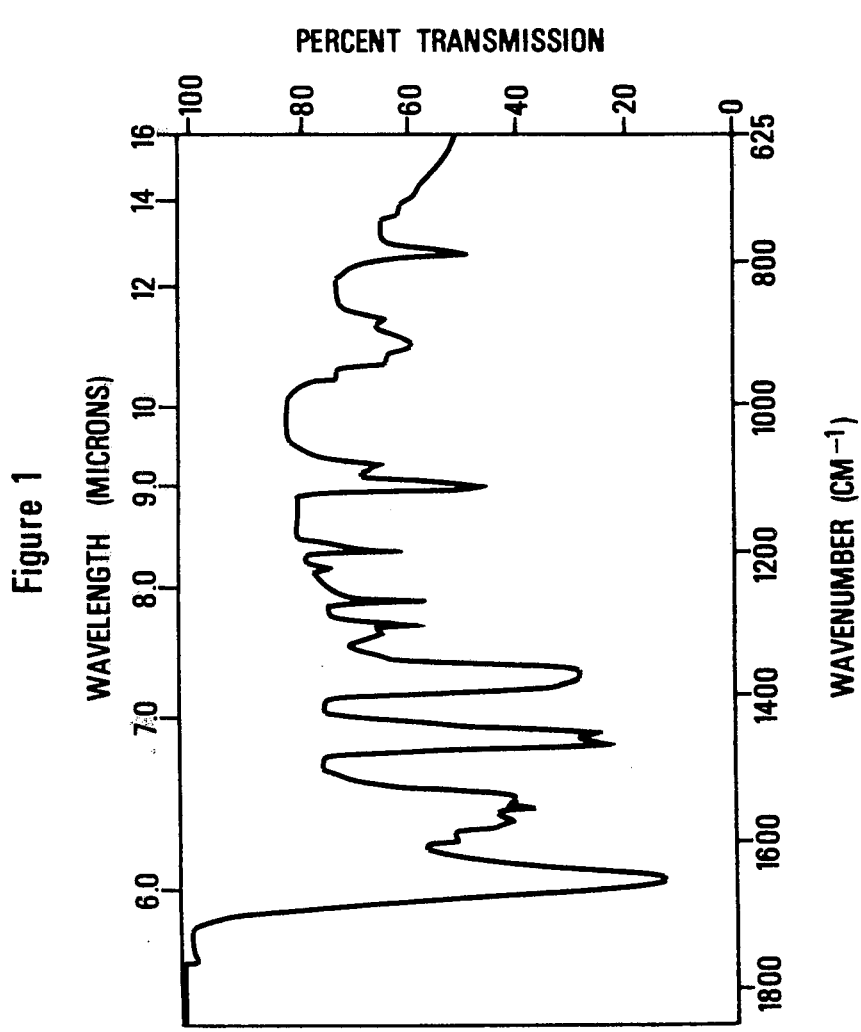

United States Patent [19]

Abdulla et al.

[11] 4,252,954

[45] Feb. 24, 1981

[54] SALTS OF DIHALO-3,4-DIHYDRO-3-OXO-2-QUINOXALINE CARBOXYLIC ACIDS AND HINDERED AMINES

[75] Inventors: Riaz F. Abdulla, Greenfield; Donald C. DeLong, Indianapolis, both of Ind.

[73] Assignee: Eli Lilly and Company, Indianapolis, Ind.

[21] Appl. No.: 88,275

[22] Filed: Oct. 25, 1979

[51] Int. Cl.$^3$ .................. A61K 31/495; C07D 241/44; C07D 403/02; C07D 209/96
[52] U.S. Cl. .................................... 544/230; 544/354; 424/250

[58] Field of Search ................. 544/354, 230; 424/250

[56] References Cited

PUBLICATIONS

Collins, et al. Chem Abs. 82, 31353q (1973).

*Primary Examiner*—Mark L. Berch
*Attorney, Agent, or Firm*—James L. Rowe; Arthur R. Whale

[57] ABSTRACT

Salts of 6,7-dihalo-3,4-dihydro-3-oxo-2-quinoxaline carboxylic acids and hindered amines, useful in combating influenza A and B.

18 Claims, 11 Drawing Figures

SALTS OF DIHALO-3,4-DIHYDRO-3-OXO-2-QUINOXALINE CARBOXYLIC ACIDS AND HINDERED AMINES

BACKGROUND OF THE INVENTION

Quinoxalines are known which have antiviral or antibacterial action. For example, Acheson, *J. Chem. Soc.* 4731 (1950) reported that p-2'-quinoxalinylaminobenzoyl-(−)glutamic acid had a small growth-inhibitory effect on L. casei. The author also prepared 2-(2-diethylaminoethyl)aminoquinoxaline, the corresponding 6,7-dichloro derivative and the corresponding diethylaminopropyl derivative but found that all of these compounds were inactive against *P. gallinaceum* in chicks. 6,7-Dichloro-2-hydroxyquinoxaline-3-carboxylic acid and its ethyl ester were prepared and used as intermediates in the production of these diethylaminoalkylaminoquinoxalines. Abdulla et al, *J. Het. Chem.*, 13, 427 (1976) used the 6,7-dichloro ester as an intermediate in the synthesis of the corresponding azeto[1,2-a]quinoxaline-1,3-dione. Belgium patent No. 769,491 (Derwent abstract 4493T supplied) discloses 2,3-dimercaptomethyl quinoxalines in which the benzene ring can be substituted with alkyl, alkoxy, halogen, trifluoromethyl, nitro, or alkylenedioxy. The compounds are said to be antiviral agents. 3,6-Diamino-2-quinoxaline carboxamides, stated to be useful as diuretics, anticonvulsant, anti-inflammatory agents, and to have antiviral activity against Herpes simplex, are disclosed in U.S. Pat. No. 3,192,212. A group of antiviral quinazolines (isomeric with quinoxalines) are disclosed in Belgium patent No. 815,196. A series of antiviral 2-chloro- or 2-hydrazinoquinoxalines are disclosed in three papers by Westphal, et al. *Pharmazie*, 32, 570–571, 687–689, 563–565 (1977). The following types of compounds were prepared: Quinoxaline- 2-ones substituted in the 3 position with a heterocyclic ring including benzimidazole, benzothiazole, or benzoxazole (no utility was given for these compounds); 2-chloro or 2-hydrazinoquinoxalines stated to be active against coxsackie B, vaccina, sindbas, and pseudorabies viruses; and, finally, a group of s-triazolo[4,3-a]quinoxalines, prepared by cyclizing a 2-hydrazinoquinoxaline, were allegedly useful against some of the above viruses.

In addition to the above listed antiviral agents having the basic quinoxaline structure, there has been a considerable amount of work carried out on quinoxaline-1,4-dioxides as antiviral agents. Much of this work is summarized in Hurst, et al., *Brit. J. Pharmacol.*, 8, 297, (1953). According to this summary, quinoxaline-1,4-dioxides were the most active compounds tested in experimental psittacosis and lymphogranuloma venereum infections. A large number of derivatives of the quinoxaline-1,4-dioxides are summarized on page 301 of the article and include compounds with the following substituents in the quinoxaline ring: ethyl, ethoxymethyl, acetoxymethyl, 2-methyl-3-ethyl, 2-methyl-3-carboethoxy, 2,3-dihydroxymethyl, 2,3-diiodomethyl, 2,3-bis(dimethylaminomethyl), etc. Substituents in the benzene ring include: halogens, alkyl, nitro, trifluoromethyl, cyano, carboethoxy, carbamyl, acetamido, etc. (see also Derwent Abstract 5641U abstracting U.K. Pat. No. 1,305,138). A similar group of quinoxaline-1,4-dioxides is disclosed in Belgian patent No. 683,206, abstracted as Derwent No. 25,122. Substituted 2-formylquinoxaline-1,4-dioxides are disclosed in U.S. Pat. No. 3,433,871. The compounds are said to be antibacterial and antiviral compounds. U.K. Pat. No. 1,308,370 discloses an improved method of making substituted quinoxaline-1,4-dioxides having a variety of substituents in the quinoxaline ring including carboxamides (page 13), esters (page 15), a third ring (page 17–21), acyl derivatives (page 21), 3-hydroxy-2-alkoxycarbonyl derivatives (page 23), hydroxy carboxamides (page 24), etc. These compounds are alleged to have in vitro activity against harmful micro-organisms. Antiviral activity is not mentioned. Another patent relating to methods of preparing quinoxaline-1,4-dioxides, is U.K. Pat. No. 1,215,815. Page 1 of this patent reviews the literature briefly. 2-Hydroxy-3-carboalkoxyquinoxaline-1,4-dioxides are named specifically. Finally, U.S. Pat. No. 3,957,387 describes a group of carboxamidoquinoxalinedioxides. The compounds are alleged to be antibacterial substances.

The above survey of antiviral quinoxalines or quinoxalines containing various substituent groups and useful as either antiviral or antibacterial agents is not exhaustive and merely exemplary of the volumninous literature on the subject. It should be noted, however, that there has not been any public disclosure of quinoxalines having antiviral activity, particularly against both Maryland B and Ann Arbor strains of influenza virus in vivo. Such activity has, however, been disclosed in the copending application of Riaz Abdulla, Ser. No. 60,445 filed July 25, 1979, abandoned.

The antiviral activity of 1-aminoadamantane (amantidine, 1-adamantylamine) was first disclosed by Davies et al. *Science*, 144, 862 (1964). 1-Adamantylamine was the first of the highly hindered amines shown to have antiviral activity. 1-Adamantylamine is said to be active against influenza virus A² strain prophylactically. The compound also may have some use in the propylaxis of Asian flu strains antigenically related to strain A². 3-Methyl-1-aminoadamantane, dl-cyclooctylamine, 2-norbornylamine and 1-adamantyl-1-aminoethane (rimantadine) have all been shown to be antiviral agents.

U.S. patents relating to the use of adamantylamines as antiviral agents include U.S. Pat. Nos. 3,310,469 (1-aminoadamantane) 3,328,251 and 3,532,748 (2-aminoadamantanes) 3,592,934 (aminomethyladamantanes including rimantidine and aminomethyltricyclo[4.3.1.1$^{3,8}$] undecanes). See also *Herba Hung.*, 7, 115 (1968) for a review of virucidal (and oncolytic) activity of adamantylamines. Again, the above listing is not exhaustive, but exemplary only.

SUMMARY OF THE INVENTION

This invention provides antiviral salts of the formula:

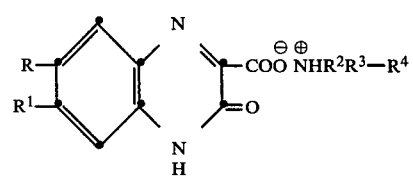

wherein R and R¹ are the same or different halogens of the group consisting of F, Cl, Br and I, R² is H, CH₃, or C₂H₅, R³ when taken singly is H, CH₃, C₂H₅, CH₂C₆H₅, C₂H₄OH or CH₂COOC₂H₅, R⁴ when taken singly is a hindered hydrocarbyl radical of the group consisting of cyclooctyl, norbornyl, Ad, and $CHR^2Ad$, and $R^3$ and $R^4$ when taken together with the nitrogen atom to which they are attached form a spiro pyrrolidine of the formula

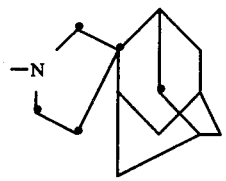

The amine moiety $NHR^2R^3$-$R^4$ is derived from a hindered hydrocarbyl amine, particularly one having virus inhibiting activity on its own against influenza virus, specifically against strains of influenza A virus. These hindered amines can be represented by the formula $NR^2R^3$-$R^4$ wherein $R^2$, $R^3$ and $R^4$ have the same meaning as hereinabove, $R^4$ when taken singly represents, among others, the cyclooctyl radical

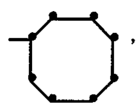

, the norbornyl (tricyclo [2.2.1] heptyl) radical

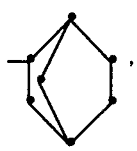

, the Ad, $—CH_2Ad$ or $—CHCH_3—Ad$ radicals wherein Ad is an 1-adamantyl (tricyclo[3.3.3.1$^{3,7}$]decyl) radical of the formula or a 4-homoisotwistane of the formula or a 2-adamantyl radical of the formula 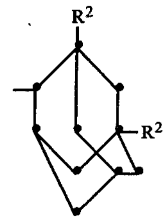 or a tricyclo[4.3.3.1$^{3,8}$]undecane radical of the formula or of the formula wherein $R^2$ has the same significance as hereinabove, and $R^3$ and $R^4$ when taken together with the nitrogen atom to which they are attached form an adamantylspiropyrrolidine represented by the formula 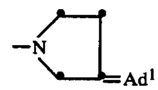 wherein $Ad^1$ is an 2-adamantyl diradical of the formula 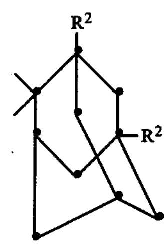 The adamantylspiropyrrolidine (spiroamine) is named systematically as a spiropyrrolidine-3,2'-tricyclo[3.3.3.1$^{3,7}$]decane or as an adamantane-2-spiro-3'-pyrrolidine.

Illustrative salts coming within the scope of this invention include salts of 6,7-dibromo-3,4-dihydro-3-oxo-2-quinoxaline carboxylic acid and the following hindered amines.

1-adamantylamine
2-adamantylamine
3,5-dimethyl-1-adamantylamine
1-methylaminoadamantane
3-dimethylaminotricyclo[4.3.3.1.$^{3,8}$] undecane
dl-cyclo-octane
1amino-1-(1-adamantyl)ethane,
1-N-methylaminoadamantane
1-N-ethylaminoadamantane
1-N-benzylaminoadamantane
1-N,N-dimehtylaminoadamantane
1-(2-hydronyethylamino)adamantane
1-(bis-2-hydronyethylamino)adamantane 1-(1-pyrrolidinyl)adamantane
1-N-adamantyl-glycine ethyl ester
N-1-adamantylazidine
3-amino-4-homoisotwistane
Salts of 6-chloro-7-bromo-3,4-dihydro-3-oxo-2-quinoxaline carboxylic acid and the following hindered amines
1-aminonorbornane
2-dimethylaminoadamantane
1-methyl-2-aminoadamantane
1-methyl-1-methylaminomethyladamantane
1-adamantylamine
Salts of 6-bromo-7-chloro-3,4-dihydro-3-oxo-2-quinoxaline carboxylic acid and the following hindered amines
1-dimethylaminoadamantane
3-aminotricyclo[4.3.3.1$^{3,8}$]undecane
1-cyclooctylamine
3-aminomethyltricyclo[4.3.3.1$^{3,8}$]undecane
3-methyl-1-adamantylamine
3,5-dimethyl-1-adamantylamine
1-adamantylamine
Salts of 6,7-dichloro-3,4-dihydro-3-oxo-2-quinoxaline carboxylic acid with the following hindered amines
1-adamantylamine
1-methyladamantane-2-spiro-3′-pyrrolidine
3,5-dimethyl-2-adamantylamine
3-methylaminomethyltricyclo[4.3.3.1$^{3,8}$]undecane
N-methyl-2-adamantylamine
Salts of 6,7-difluoro-3,4-dihydro-3-oxo-2-quinoxaline carboxylic acid with the following hindered amines
1-norbornylamine
1-adamantylamine
2-methylaminoadamantane
1-dimethylamino-3-methyladamantane
d-cyclo-octylamine, and
Salts of the 6,7-di-iodo-3,4-dihydro-3-oxo-2-quinoxaline carboxylic acid with the following hindered amines
1-adamantylamine
1-methyl-spiropyrrolidine-3,2′-tricyclo[3.3.3.1.$^{3,7}$]decane
1-norborylamine
1-methylaminomethyltricyclo[4.3.3.1$^{3,8}$]undecane
2-dimethylaminomethyladamantane rimantidine The salts of this invention do not behave as do classic salts such as NaCl, particularly in less polar solvents; i.e., 66 percent aqueous DMF (dimethylformamide), as compared to water. For example, titration of the salt of 6,7-dibromo-3,4-dihydro-3-oxo-2-quinoxaline carboxylic acid and 1-adamantylamine in 66 percent aqueous DMF yield an apparent pKa of about 3.6 for the acid component, but the free acid in the same solvent has an apparent pKa of 4.2. The apparent pKa for the amine is about the same whether in the salt or as the free base. A spectrophotometric determination of the apparent pKa's of the acid component give 2.7 for the salt but 4.0 for the free acid. An examination of the ultraviolet spectral shifts with changing pH indicates that, in water, the same ionic species are present for the acid component in the salt or as the free acid. In 66 percent aqueous DMF, however, there are appreciable differences in the pH profile. All of the above results indicate some complex interaction (such as tight ion-pair formation) between the ionic components of the salt (beyond simple charge neutralization) is taking place. Some of the properties of the salts of this invention, particularly relating to their oral efficacy, may be attributable to such complex interaction.

The preparation of the salts of this invention is illustrated by the following specific examples.

EXAMPLE 1

Preparation of 6,7-dibromo-3,4-dihydro-3-oxo-2-quinoxaline carboxylic acid 1-adamantylamine salt Two grams of 6,7-dibromo-3,4-dihydro-3-oxo-2-quinoxaline carboxylic acid were dissolved in 100 ml. of anhydrous N,N-dimethylformamide (DMF). 0.87 g. of 1-adamantylamine was added with stirring. After the addition had been completed, the reaction mixture was stirred at about 100° C. for two hours, cooled to room temperature and then stirred at that temperature overnight. The reaction mixture was filtered and the filter cake dried at 90° C. at 10 mm of mercury for one hour. 6,7-dibromo-3,4-dihydro-3-oxo-2-quinoxaline carboxylic acid 1-adamantylamine salt thus prepared had the following physical and chemical characteristics:

Analysis calculated; C, 45.53; H, 4.63; N, 8.38. Found: C, 45.35; H, 4.42; N, 8.57.
Mass spectrum; m/e at 346,151.
Infrared spectrum (Nujol Mull) see FIG. 1.

Following the above procedure, but substituting 3-methyl-1-adamantylamine for 1-adamantylamine, there was prepared a salt of 6,7-dibromo-3,4-dihydro-3-oxo-2-quinoxaline carboxylic acid and 3-methyl-1-adamantylamine. The crystalline product was isolated by filtration and dried; melting point=280°–282° C. with decomposition.

Figure 2:
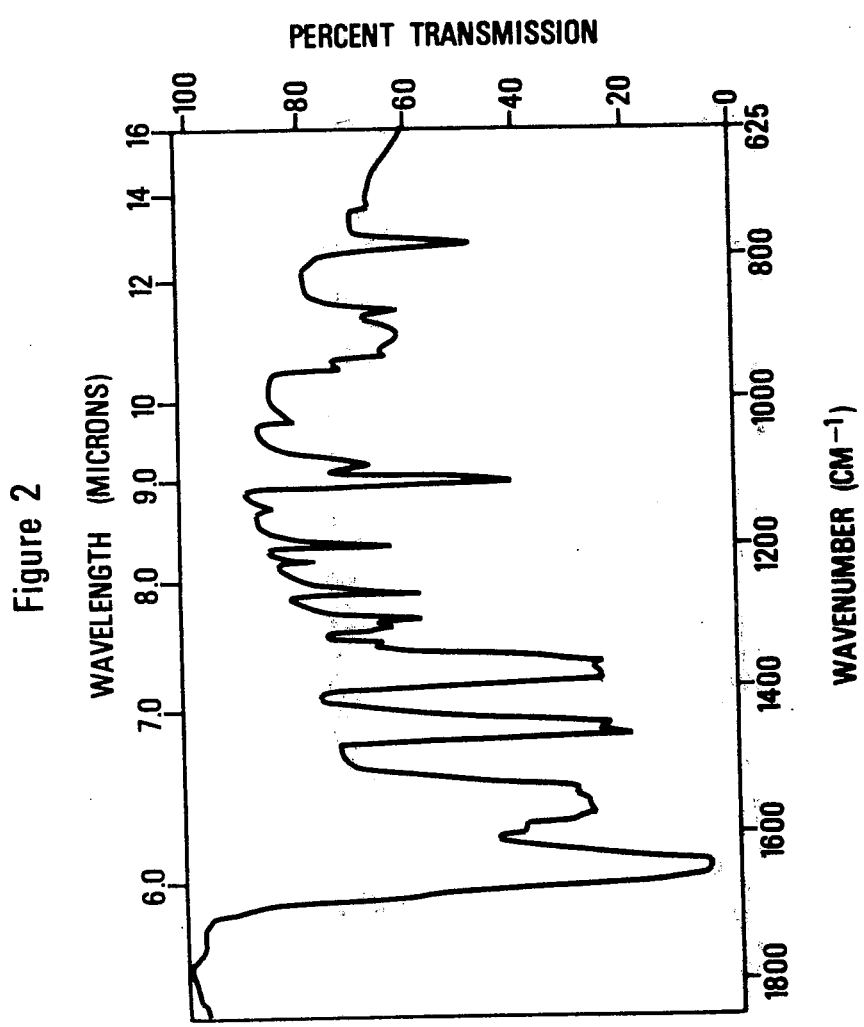

Analysis calculated; C, 46.90; H, 4.33; N, 8.20; Br, 31.20. Found: C, 47.20; H, 4.60; N, 7.91; Br, 30.72.
Infrared (Nujol Mull) see FIG. 2.

The 3-methyl-1-adamantylamine starting material was isolated from its hydrochloride salt by dissolving the hydrochloride in water, adjusting the pH to about 12 with 1 N aqueous sodium hydroxide and extracting the free base into dichloromethane. The dichloromethane solution was separated and the solvent stripped to give the desired free base.

Following the above procedure, 6,7-dichloro-3,4-dihydro-3-oxo-2-quinoxaline carboxylic acid was reacted with 3-methyl-1-adamantylamine to yield the 3-methyl-1-adamantylamine salt of 6,7dichloro-3,4-dihydro-3-oxo-2-quinoxaline carboxylic acid. The compound melted at about 288° C. with decomposition.

Figure 3:
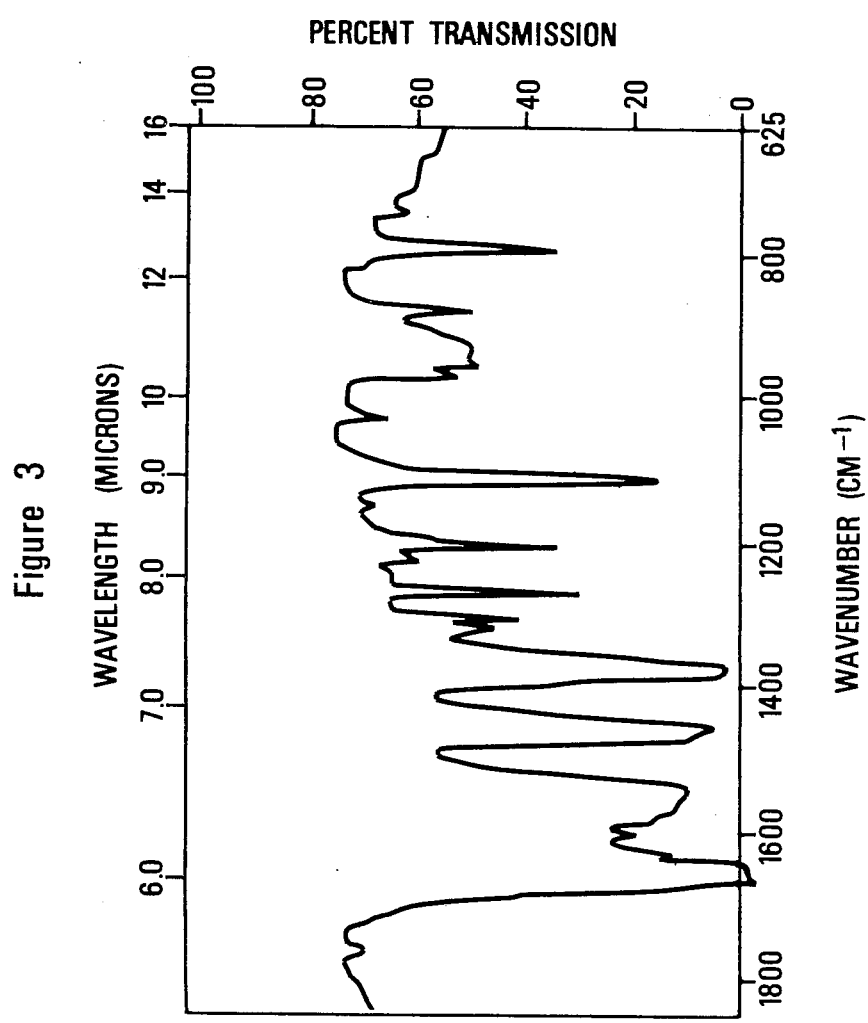

Analysis calculated; C, 56.75; H, 5.24; N, 9.93; Cl, 16.75. Found: C, 56.45; H, 5.48; N, 9.99; Cl, 17.01.
Infrared spectrum (Nujol Mull) see FIG. 3.

The following additional salts of 6,7-dichloro-3,4-dihydro-3-oxo-2-quinoxaline carboxylic acid were prepared.

(a) cyclooctylamine salt, melting at 242° C. with decomposition

Figure 4:
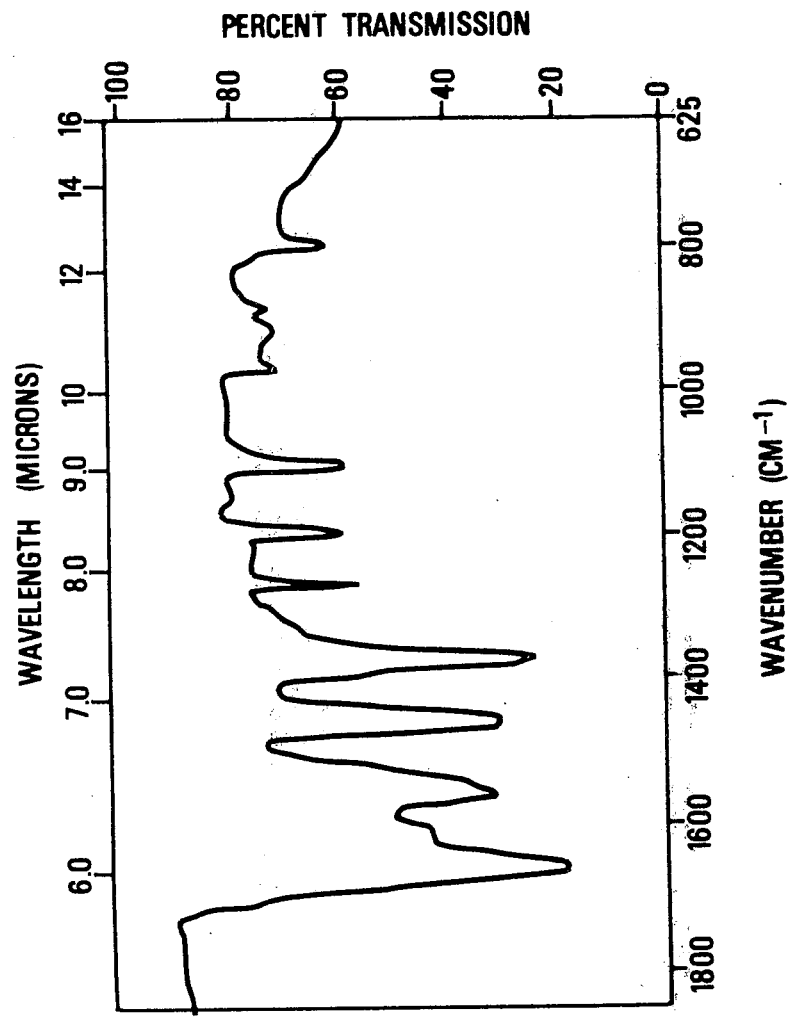

Analysis calculated; C, 52.86; H, 5.48; N, 10.88; Cl, 18.36. Found: 52.64; H, 5.33; N, 10.81; Cl, 18.62.
Infrared spectrum (Nujol Mull) see FIG. 4.

Figure 5:
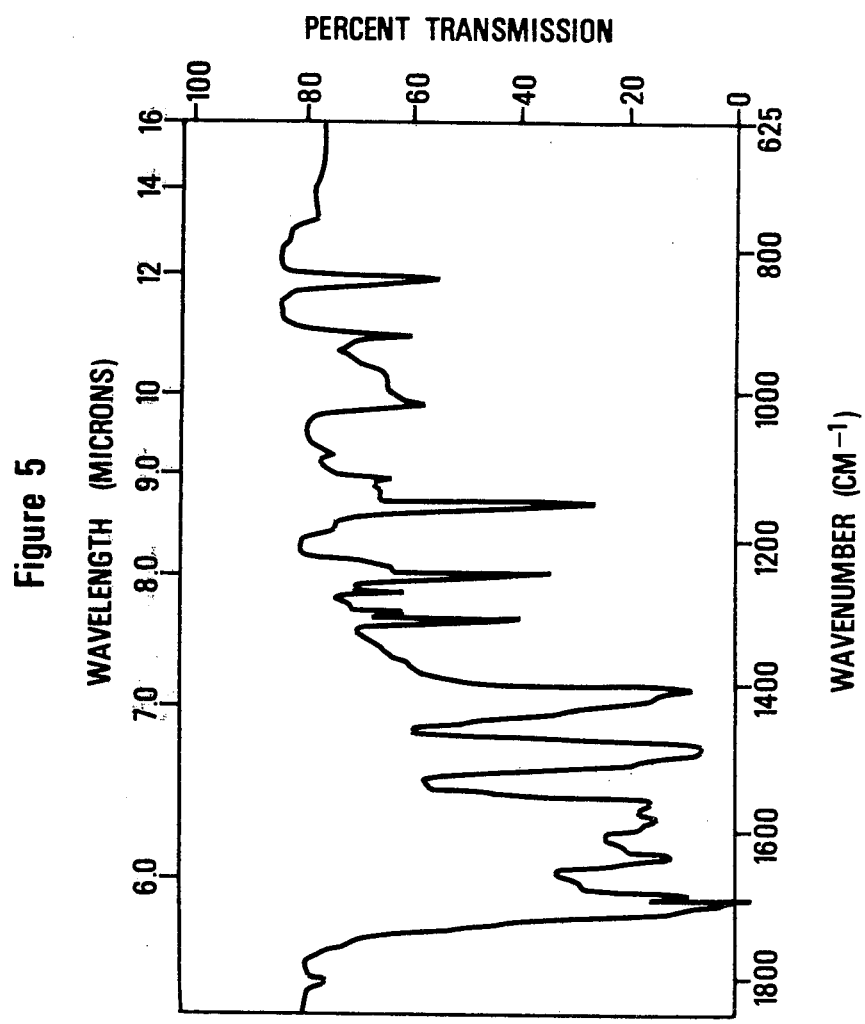

(b) rimantadine [1-(1-adamantyl)-1-aminoethane], salt melting at 275° C. with decomposition Analysis calculated; C, 57.54; H, 5.75; N, 9.59; Cl, 16.18. Found: C, 57.26; H, 5.69; N, 9.83; Cl, 16.16.
Infrared spectrum (Nujol Mull) see FIG. 5.

Figure 6:
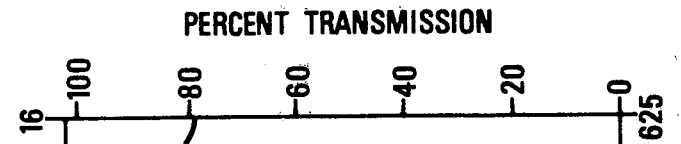

(c) spiroamine (1-methylspiropyrrolidine-3,2′-tricyclo[3.3.1.1$^{3,7}$]decane)salt, melting at about 228° C. with decomposition Analysis calculated; C, 59.49; H, 5.86; N, 9.05; Cl, 15.27. Found: C, 59.59; H, 5.60; N, 9.22; Cl, 15.06.
Infrared spectrum (Nujol Mull) see FIG. 6.

(d) 1adamantylamine salt melting at about 295° C. with decomposition.

Figure 7:
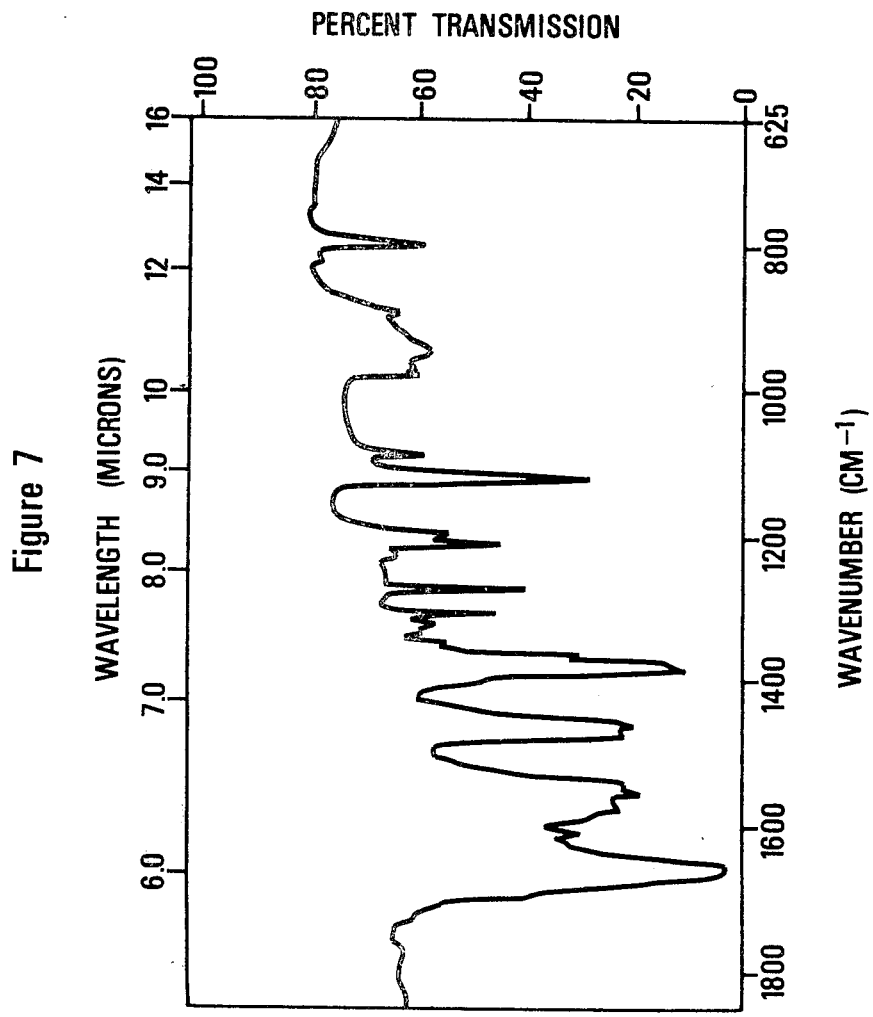

Analysis calculated; C, 55.62; H, 5.16; N, 10.24; Cl, 17.28. Found: C, 55.48; H, 5.17; N, 10.49; Cl, 17.07.

nInfrared spectrum (Nujol Mull) see FIG. 7.

These additional salts of 6,7-dibromo-3,4-dihydro-2-oxo-3-quinoxaline carboxylic acid were prepared.

(a) Rimantadine salt melting at about 281° C. with decomposition.

Analysis calculated; C, 47.84; H, 4.78; N, 7.97; Br, 30.31. Found: C, 47.58; H, 4.51; N, 8.21; Br, 30.43.

Figure 8:
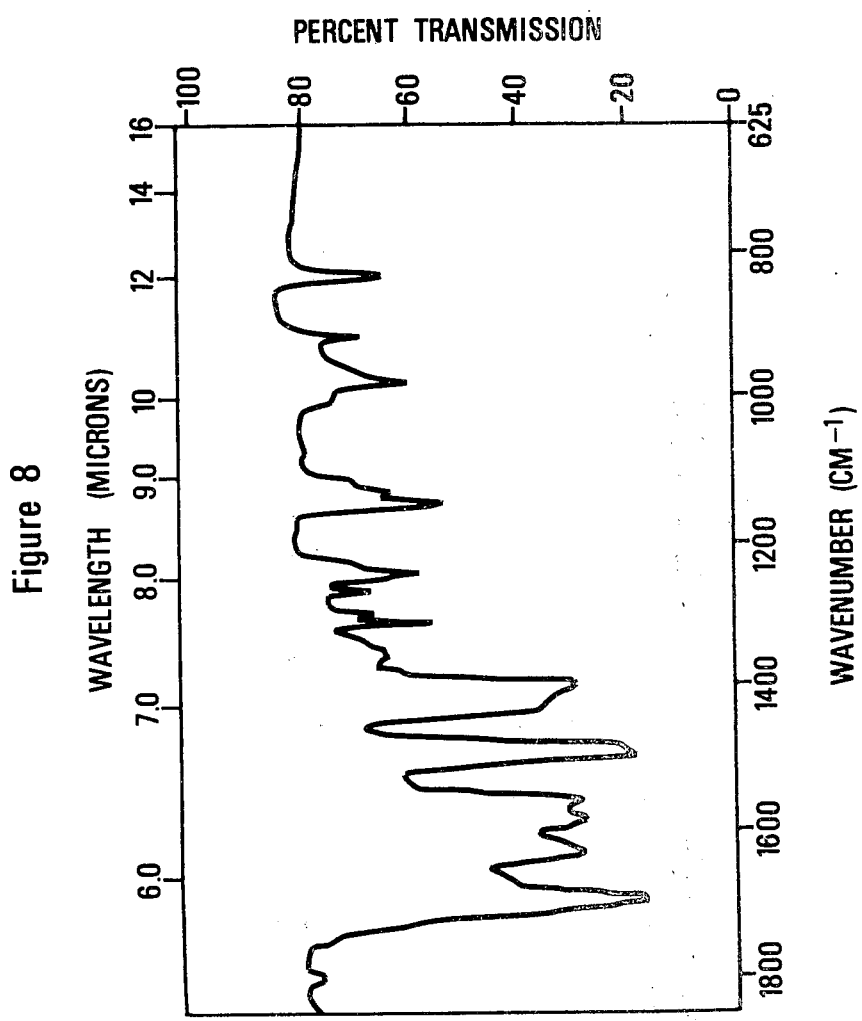

Infrared spectrum see FIG. 8.

(b) Spiroamine salt melting at about 225° C. with decomposition

Analysis calculated; C, 49.93; H, 4.92; N, 7.59; Br, 28.88. Found: C, 49.67; H, 4.62; N, 7.65; Br, 29.14.

Figure 9:
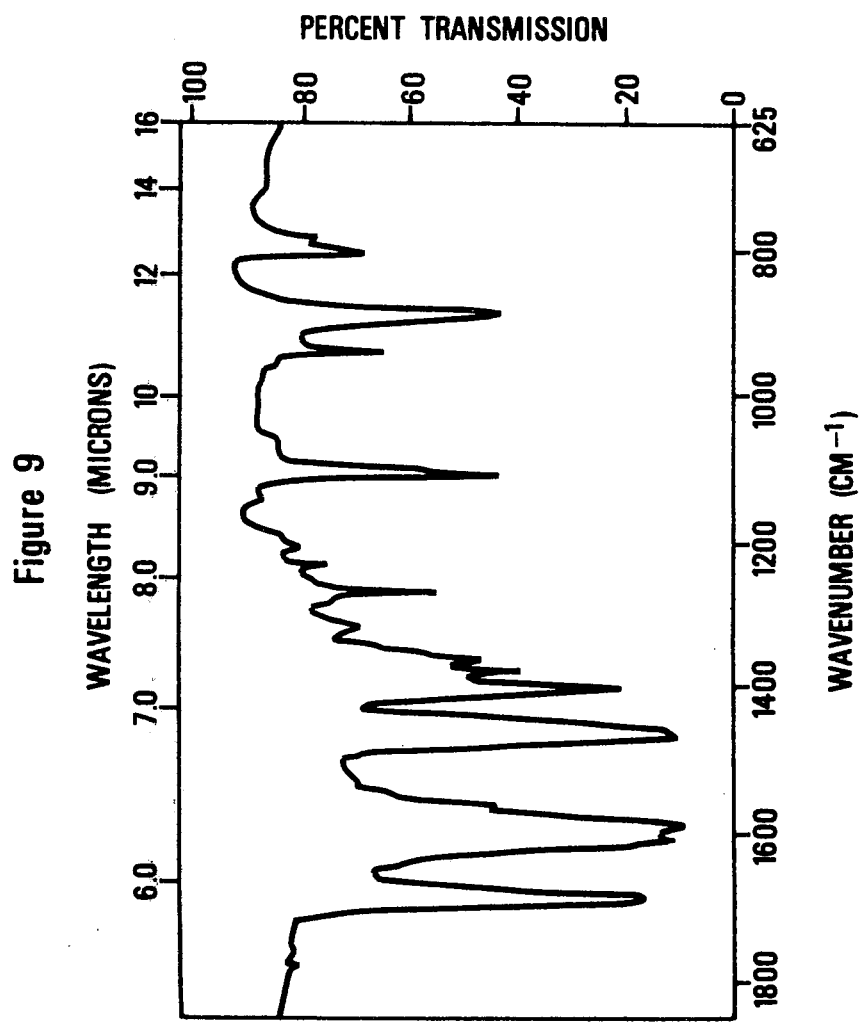

Infrared spectrum see FIG. 9.

(c) Cyclo-octylamine salt melting at about 245° C. with decomposition

Analysis calculated; C, 42.97; H, 4.45; N, 8.74; Br, 33.63. Found: C, 42.70; H, 4.36; N, 8.55; Br, 33.80.

Figure 10:
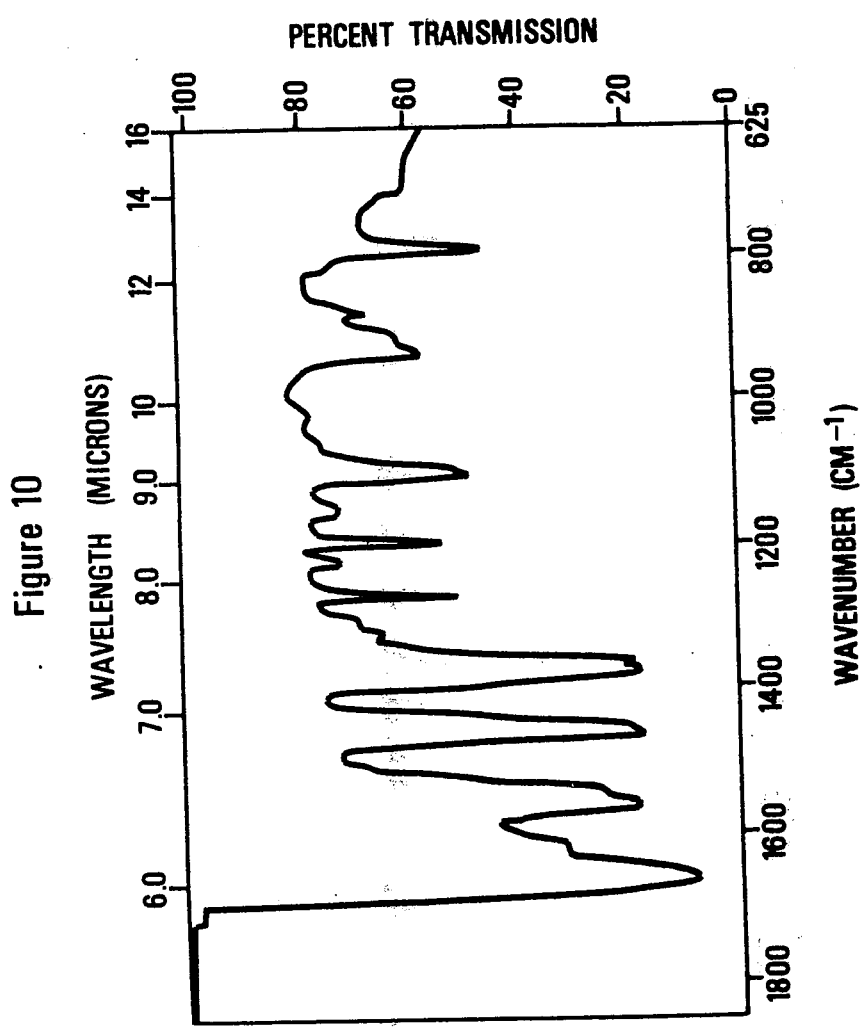

Infrared spectrum (Nujol Mull) see FIG. 10.

The 1-adamantylamine salt of 6,7-difluoro-3,4-dihydro-3-oxo-2-quinoxalinecarboxylic acid was prepared.

Melting point=286°-288° C.

Figure 11:
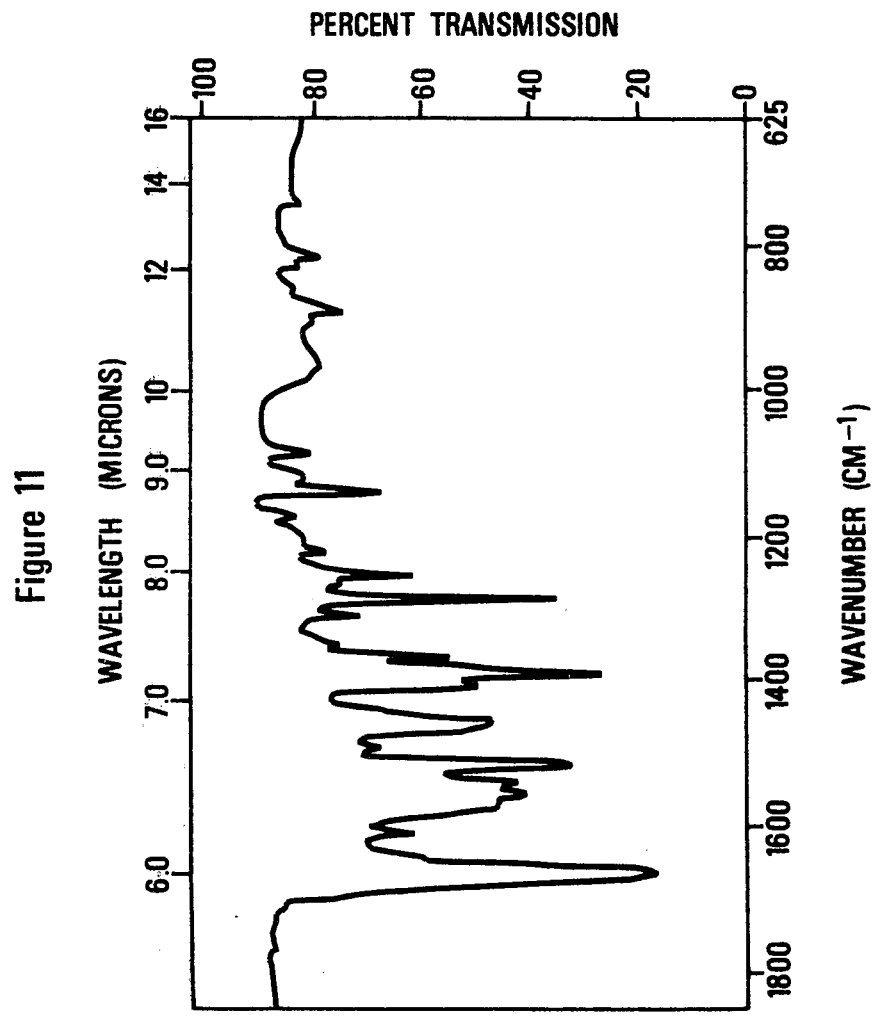

Infrared spectrum (Nujol Mull) see FIG. 11.

The hindered amine components of the antiviral salts of this invention are known compounds. Several are commercially available including 1-aminoadamantane (1-adamantylamine 1-amino-tricyclo[3.3.3.1$^{3,7}$]decane) dl-cyclo-octylamine, and 2-norbornylamine (2-aminobicyclo[2.2.1]heptane), 1-methylaminoadamantane and 1-(1-adamantyl)-1-aminoethane. Other hindred amines including 1-ethylaminoadamantane, 1-dimethylaminoadamantane, 1-amino-3,5,7-trimethyladamantane, 1-amino-3,5-dimethyladamantane 2-adamantaneamine, and the like are readily preparable from procedures available in the art. See for example U.S. Pat. Nos. 3,592,934, 3,532,748, 3,152,180, 3,450,761, 3,283,001, 3,310,469 and the following early references: Stettler et al, Ber., 93, 760(1963), Gerzon et al. *J. Med. Chem*, 6, 760(1963).

The quinoxalinone carboxylic acid components of the salts of this invention can be prepared by reacting a suitably substituted o-phenylenediamine with a dialkyl 2-ketomalonate (a dialkyl mesoxalate). The reaction is carried out in a mutual anhydrous solvent, customarily at reflux temperature of the solvent and is illustrated below in the following reaction scheme:

REACTION SCHEME I

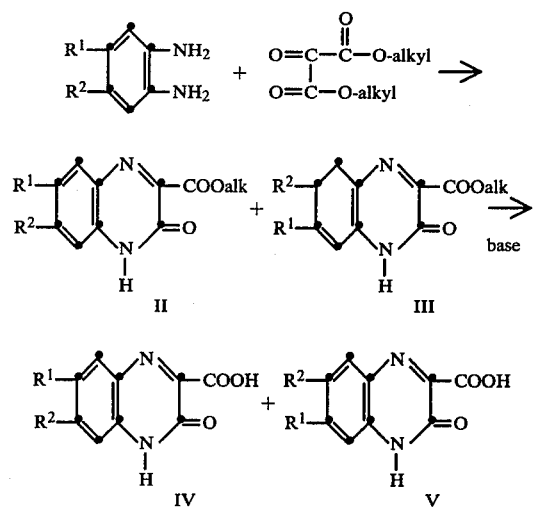

According to Reaction Scheme I, if $R^1$ and $R^2$ are the same halogen i.e., I, F, Cl or Br, only one ester (represented by either II or III) will result and only one carboxylic acid (IV or V). If the starting o-phenylenediamine is unsymmetrically substituted; however; i.e., $R^1$ and $R^2$ are not identical, a mixture of isomeric esters will result, as represented by formulas II and III and a mixture of free carboxylic acids, as represented by formulas IV and V.

In the above reaction scheme, when $R^1$ and $R^2$ are different halogens, the product of the reaction of the substituted o-phenylenediamine and diethyl mesoxalate is a mixture of compounds represented by formulas II and III above.

A reaction procedure for the unequivocal synthesis of a given quinoxalinone carboxylic acid is illustrated in Reaction Scheme 2 below:

Reaction Scheme 2

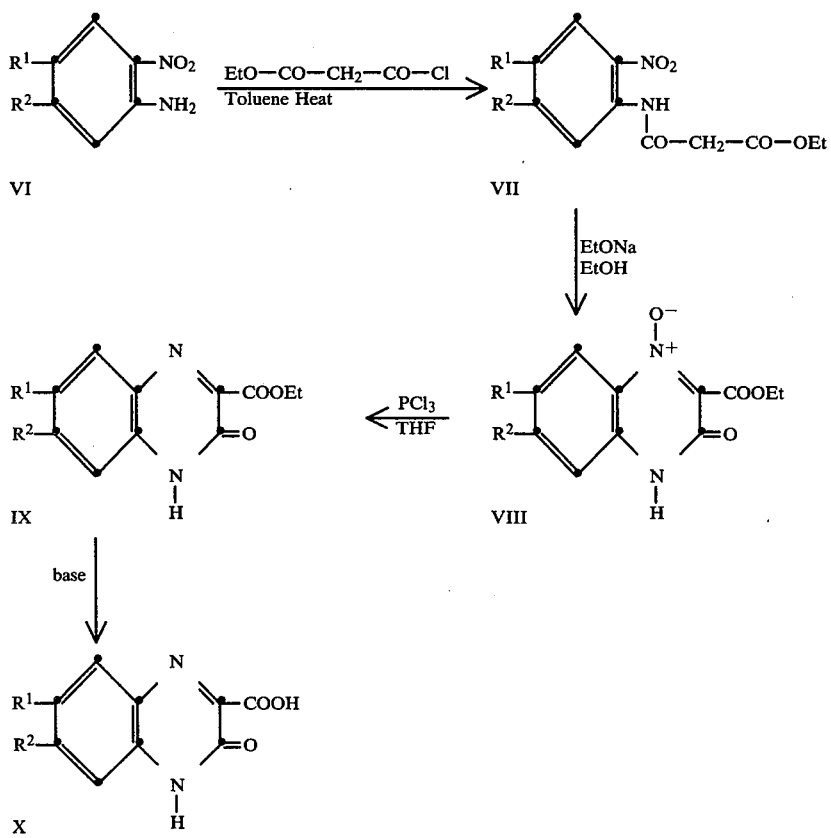

in which $R^1$ and $R^2$ have their previously assigned meaning.

According to Reaction Scheme 2, a 2-nitro-4,5-disubstituted aniline (VI) is reacted with ethyl malonyl chloride (or other alkyl malonyl halide) to give the corresponding ethyl malonyl amide derivative on the aniline nitrogen (VII). A base catalyzed annelation using sodium ethoxide at 0° C. yields the quinoxaline $N^1$-oxide (VIII), treatment of which with phosphorus trichloride in tetrahydrofuran (THF) at ambient temperature produces unambiguously a 6,7-disubstituted-3,4-dihydro-3-oxo-2-quinoxaline carboxylate, ethyl ester (IX). Base hydrolysis of this carboxylate ester yields the desired carboxylic acid X.

The preparation of the above compounds is illustrated by the following specific examples:

Preparation of 2-oxo-3-quinoxaline carboxylate esters and the corresponding carboxylic acids is illustrated below.

PREPARATION 1

Ethyl 6,7-Dichloro-3,4-dihydro-3-oxo-2-quinoxaline Carboxylate.

A solution of 17.7 g. of 4,5-dichloro-o-phenylenediamine and 200 ml. of anhydrous ethanol was prepared. A 17.4 g. batch of diethyl 2-keto-malonate was added to this solution and the mixture was heated to refluxing temperature for about 17 hours. The volatile constituents were removed by evaporation in vacuo. Recrystallization of the residue from ethanol yielded 20 g. of ethyl 6,7-dichloro-3,4-dihydro-3-oxo-2-quinoxaline carboxylate formed in the above reaction; melting in the range 226°-227° C.

PREPARATION 2

Ethyl 6-Chloro-7-bromo-3,4-dihydro-3-oxo-2-quinoxaline Carboxylate.

Five grams of 2-nitro-4-bromo-5-chloro-aniline were dissolved in 150 ml. of benzene. Five grams of the acid chloride of monoethyl malonate were added with stirring under a nitrogen atmosphere. The reaction mixture was heated to refluxing temperature overnight. Thin-layer chromatography indicated that the reaction was essentially complete at this time. The reaction mixture was cooled and the benzene removed by evaporation in vacuo. The residue containing N-ethoxycarbonylacetyl 2-nitro-4-bromo-5-chloro-aniline formed in the above reaction, was recrystallized from anhydrous ethanol to yield fluffy yellow crystals melting at 119°-121° C.

Sodium ethoxide was prepared under anhydrous conditions from 35 ml. of anhydrous ethanol and 1 g. of sodium in a nitrogen atmosphere. The mixture was stirred until the sodium was dissolved completely after which time the mixture was chilled to about 0° C. N-ethoxycarbonylacetyl 2-nitro-4-bromo-5-chloroaniline was added and the resulting mixture was stirred at 0° C. for about 3 hours. The reaction was then quenched by adding it to 300 ml. of 1 N aqueous hydrochloric acid at 0° C. This aqueous mixture was stirred until a solid precipitate formed. The precipitate was separated by filtration, dried, and the filter cake was recrystallized from anhydrous ethanol. Ethyl 6-chloro-7-bromo-3- oxo-2-quinoxaline carboxylate N-oxide thus prepared melted at 219°-221° C.; yield=2 g.

Analysis Calc.; C, 38.01; H, 2.32; N, 8.06. Found: C, 37.79; H, 2.35; N, 8.24.

One gram of ethyl 6-chloro-7-bromo-3,4-dihydro-3-oxo-2-quinoxaline carboxylate N-oxide was dissolved in 50 ml. of THF. Six ml. of phosphorus trichloride were added and the resulting mixture heated gently at refluxing temperature overnight. The reaction mixture was poured into 500 ml. of an ice-water mixture. A solid, comprising ethyl 6-chloro-7-bromo-3,4-dihydro-3-oxo-2-quinoxaline carboxylate formed in the above reaction, was separated by filtration; melting point=203°-205° C.; yield=0.6 g.

PREPARATION 3

Ethyl 6,7-Difluoro-3,4-dihydro-3-oxo-2-quinoxaline Carboxylate.

About 25 ml. of acetic anhydride were added cautiously to 25.8 g. of 3,4-difluoroaniline. The mixture was stirred for 1 hour after the addition was complete and was then poured over ice. The resulting white precipitate comprising 3,4-difluoroacetanilide was separated by filtration, and dried. Recrystallization from a benzene-acetone solvent mixture yielded 30 g. of 3,4-difluoroacetanilide melting at 125°-6° C.

Analysis Calc.; C, 56.14; H, 4.12; N, 8.12. Found: C, 56.28; H, 4.22; N, 8.16.

A solution of 8.5 g. of 3,4-difluoroacetanilide was prepared in 50 ml. of 18 M sulfuric acid, and was chilled to about 0° C. A 10.5 g. portion of propyl nitrate was added in dropwise fashion. The consequent reaction mixture was stirred at about 0° C. for two hours and was then poured over an ice-water mixture. A pale yellow precipitate comprising 4,5-difluoro-2-nitroacetanilide formed in the above reaction was separated by filtration. The filter cake was washed several times with water and then recrystallized from an ethanol-water solvent mixture (yield=9 g.). The compound melted at 105°-107° C.

Analysis Calc.; C, 44.46; H, 2.80; N, 12.96. Found: C, 44.24; H, 2.76; N, 12.88.

A mixture of 6.51 g. of 4,5-difluoro-2-nitroacetanilide and 100 ml. of 6 N aqueous hydrochloric acid was heated to refluxing temperature for about 2 hours. The reaction mixture was then cooled. Crystals which formed were separated by filtration, and the separated crystals were washed with water, dried, and recrystallized from a hexane-dichloromethane solvent mixture. A yield of 5.0 g. of 4,5-difluoro-2-nitroaniline was obtained, melting at 106°-108° C.

Analysis Calc.; C, 41.39; H, 7.32; N, 16.07. Found: C, 41.41; H, 7.35; N, 15.85.

A reaction mixture was prepared containing 8.75 g. of 4,5-difluoro-2-nitroaniline, 200 ml. of ethanol, and as a catalyst 1 g. of 10 percent palladium-on-carbon. The mixture was hydrogenated until the theoretical amount of hydrogen had been absorbed, using a low-pressure hydrogenation apparatus. The catalyst was separated by filtration using standard precautions and the product of the reaction, 4,5-difluoro-o-phenylenediamine, was reacted with diethyl mesoxalate following the procedure of Preparation 1 without further purification. The product of this reaction, ethyl 6,7-difluoro-3,4-dihydro-3-keto-2-quinoxaline carboxylate, melted at about 193°-195° C.

PREPARATION 4

6,7-Difluoro-3,4-dihydro-3-oxo-2-quinoxaline Carboxylic Acid.

To 2.42 g. of ethyl 6,7-difluoro-3,4-dihydro-3-oxo-2-quinoxaline carboxylate were added 50 ml. of 2 N aqueous sodium hydroxide. The mixture was heated to refluxing temperature for 3 hours and was then treated with charcoal, cooled, and filtered. The filtrate containing 6,7-difluoro-3,4-dihydro-3-oxo-2-quinoxaline carboxylic acid formed in the above reaction was acidified with 12 N aqueous hydrochloric acid. The acid, being insoluble in the aqueous acidic mixture, precipitated and the precipitate was separated by filtration. The filter cake was crystallized from an ethanol-acetone solvent mixture to yield 1.3 g. of 6,7-difluoro-3,4-dihydro-3-oxo-2-quinoxaline carboxylic acid melting at 220°-225° C.

Analysis Calc.; C, 47.80; H, 1.78; N, 12.39. Found: C, 47.73; H, 1.94; N, 12.63.

PREPARATION 5

Ethyl 6,7-Di-iodo-3,4-dihydro-3-oxo-2-quinoxaline Carboxylate

A reaction mixture was prepared containing 76 g. of 20% oleum, 10 g. of iodine and 10 g. of o-dinitrobenzene. The reaction mixture was stirred at a temperature in the range 170°-175° C. for 2 hours and was then cooled. The cooled reaction mixture was poured onto ice and then filtered. The filter cake, comprising 1,2-dinitro-4,5-di-iodobenzene formed in the above reaction, was dissolved in 1 l. of ether. The ether solution was washed with aqueous bisulfite and saturated aqueous sodium bicarbonate, and then dried. The ether was removed therefrom in vacuo, and the crude solid residue crystallized from ethanol to yield brownish plates consisting of 1,2-dinitro-4,5-di-iodobenzene melting at 177°-178° C.

A solution was prepared from 3 gms. of 1,2-dinitro-4,5-di-iodobenzene in 150 ml. of ethanol. Gaseous ammonia was passed into the solution while heating to refluxing temperature. This procedure was continued until TLC indicated that all starting material had reacted (about 8 hours). The volume of the solution was then reduced to ⅓ of the original volume and the solution was cooled. 2-nitro-4,5-di-iodoaniline formed in the above reaction precipitated and was collected by filtration; mp=196°-7° C.; yield=1.70 g.

Analysis Calc.; C, 18.48; H, 1.03; N, 7.18. Found: C, 18.65; H, 1.08; N, 7.33.

A reaction mixture was prepared from 1.2 g. of 2-nitro-4,5-di-iodoaniline, 1.8 g. of stannous chloride and 10 ml. of 12 N aqueous hydrochloric acid. The reaction mixture was heated to a temperature in the range 80°-100° C. with stirring. The original deep yellow color of the solution was soon discharged. After 2 hours of heating and stirring, the reaction mixture was dumped into a mixture of 100 ml. of water and 25 ml. of aqueous sodium hydroxide. A tan solid consisting of 4,5-di-iodo-o-phenylenediamine precipitated and was collected by filtration; yield=0.9 g.

A solution was prepared from 0.9 g. of 4,5-di-iodo-o-phenylenediamine and 25 ml. of ethanol. Five grams of diethyl ketomalonate were added and the resulting mixture was heated to refluxing temperature with stirring overnight. The reaction mixture was then cooled. Ethyl 6,7-di-iodo-3,4-dihydro-3-oxo-2-quinoxaline carboxylate formed in the above reaction precipitated and was collected by filtration; yield=0.8 g.; mp=275°–276° C.

Analysis Calc.; C, 28.09; H, 1.70; N, 5.96. Found: C, 28.01; H, 1.72; N, 6.07.

PREPARATION 6

Hydrolysis of Ethyl 6,7-Dichloro-3,4-dihydro-2-oxo-3-quinoxaline Carboxylate.

One gram of ethyl 6,7-dichloro-3,4-dihydro-2-oxo-3-quinoxaline carboxylate was dissolved in a mixture of 25 ml. of isopropanol and 75 ml. of water. Five grams of potassium hydroxide was added and the resulting mixture heated to reflux temperature for 5 minutes. The hot reaction mixture was decolorized with activated charcoal and filtered. The filtrate was acidified with 12 N aqueous hydrochloric acid. Needle-like yellow crystals precipitated comprising 6,7-dichloro-2-oxo-3-quinoxaline carboxylic acid formed in the above hydrolysis. The acid was collected by filtration. Other esters produced by the procedure of Preparations 1–5 and 7–8 were hydrolysed in similar fashion to yield the corresponding carboxylic acids.

PREPARATION 7

Ethyl 6,7-dibromo-2,3-dihydro-3-oxoquinoxaline Carboxylate.

Ten g. of 3,4-dibromoaniline were mixed with 40 ml. of acetic anhydride. The resulting reaction mixture was heated to a temperature in the range 100°–105° C. for one hour after which time it was poured over a mixture of ice and water. After stirring overnight, the aqueous mixture yielded an off-white precipitate weighing 11.5 g. and melting at 90°–95° C. comprising 3,4-dibromoacetanilide.

2.5 g. of 3,4-dibromoacetanilide were mixed with 8 ml. of 18 N aqueous sulfuric acid at 0° C. 1.5 g. of propyl nitrate were added while maintaining the reaction temperature in the range 0°–2° C. The chilled reaction mixture was stirred for one hour in the same temperature range and then poured over an ice-water mixture. A yellow solid comprising 4,5-dibromo-2-nitroacetanilide formed in the above reaction precipitated and was collected by filtration. Recrystallization from ethanol yields 1.2 g. of 3,4-dibromo-6-nitroacetanilide melting at 140°–141° C.

One gram of 4,5-dibromo-2-nitroacetanilide was heated to refluxing temperature for 30 minutes with 30 ml. of 6 N aqueous hydrochloric acid. The reaction mixture was then poured over an ice-water mixture and stirred. The pH of the solution was adjusted to 12 with alkali. The resulting bright yellow precipitate was separated by filtration, washed and dried; yield=0.85 g of 4,5-dibromo-2-nitroaniline melting at 204°–205° C.

Five grams of 4,5-dibromo-2-nitroaniline were suspended in 200 ml. of anhydrous ethanol to which was added about 10 g. of Raney Nickel. The hydrogenation mixture was placed in a low pressure hydrogenation apparatus at a hydrogen pressure of 55 psi. A rapid uptake of hydrogen occurred which ceased after about 25 minutes, at which time the deep yellow color originally present was discharged indicating complete reduction of the nitro group to an amine group. The hydrogenation was continued for another half hour and the hydrogenation mixture was then worked up by filtering off the catalyst, washing the filtered catalyst, and stripping the volatile constituents from the filtrate. A yield of 4.1 g. of 4,5-dibromo-o-phenylenediamine was obtained.

4,5-Dibromo-o-phenylenediamine was cyclized to the corresponding quinoxaline carboxylic acid ester by the procedure of Preparation 1 utilizing 4.1 g. of the diamine and 2.7 g. of diethyl ketomalonate in 75 ml. of anhydrous ethanol. Ethyl 6,7-dibromo-3,4-dihydro-3-oxo-2-quinoxaline carboxylate thus prepared melted at 235°–236° C. (yield=3.9 g.).

PREPARATION 8

Ethyl 6(7)-Chloro-7(6)-bromo-3,4-dihydro-3-oxo-2-quinoxaline Carboxylate.

3-Chloro-4-bromoacetanilide prepared by the procedure of Preparation 7 was nitrated in 18 M aqueous sulfuric acid with propyl nitrate at 0° C. according to the procedure of Example 7. The product of reaction was worked up by adding it to a mixture of ice and water with stirring. A yellow powder comprising 4-bromo-5-chloro-2-nitroacetanilide precipitated and was collected by filtration. Recrystallization from ethanol gave crystals melting at 128°–130° C.; yield=38 g.

4-Bromo-5-chloro-2-nitroacetanilide was hydrolyzed to the free amine by the process of Preparation 3. Reduction of 5 g. of 4-bromo-5-chloro-2-nitroaniline thus formed with Raney nickel by the procedure of Preparation 7 yielded 3.35 g. of 4-bromo-5-chloro-o-phenylenediamine. A 1.66 g. portion of the diamine was reacted with 0.85 g. of diethyl ketomalonate by refluxing in a mutual solvent for 2.5 hours. Yellow, needle-like crystals comprising ethyl 6(7)-chloro-7(6)-bromo-3,4-dihydro-3-oxo-2-quinoxaline carboxylate precipitated and were collected by filtration; mp=185°–195° C.; yield=111 g.

The salts of this invention are active both in vitro and in vivo against both A and B strains of influenza virus, Maryland B and Ann Arbor.

In vivo activity was determined as follows: White Swiss female mice (11–13 g.) McAllister strain were infected with aqueous dilutions of the Ann Arbor strain of influenza virus in air borne injection apparatus. Graded dose levels of the drug were injected intraperitoneally (IP) or administered orally by gavage 24 and 4 hours preinfection and 24 and 48 hours post-infection. Control groups were given only the pharmaceutical extending medium. The drug was administered in water containing 2% of a surfactant. The mean day of death for the treated and untreated mice was recorded and the number of survivors out of the total number of mice at each dose level also recorded. In addition a survival index was computed. The survival index is a composite measure of effectiveness incorporating both time of death, the number of survivors into a single variable in accordance with the procedure of Redman et al. *Antimicrobial Agents and Chemotherapy* 497 (1966). For convenience in listing the results of the in vivo determinations in Table 1, a letter designation has been given to each of the eleven salts of the specific examples as follow:

A. 6,7-dibromo-3,4-dihydro-3-oxo-2-quinoxaline carboxylic acid 1-adamantylamine salt.

B. 6,7-dibromo-3,4-dihydro-3-oxo-2-quinoxaline carobxylic acid, 3-methyl-1-adamantylamine salt C. 6,7-dichloro-3,4-dihydro-3-oxo-2-quinoxaline carboxylic acid, 3-methyl-1-adamantylamine salt D. 6,7-dichloro-3,4-dihydro-3-oxo-2-quinoxaline carboxylic acid, cyclooctylamine salt E. 6,7-dichloro-3,4-dihydro-3-oxo-2-quinoxaline carboxylic acid, rimantadine salt F. 6,7-dichloro-3,4-dihydro-3-oxo-2-quinoxaline carboxylic acid, spiroamine salt.
G. 6,7-dichloro-3,4-dihydro-3-oxo-2-quinoxaline carboxylic acid, 1-adamantylamine salt
H. 6,7-dibromo-3,4-dihydro-3-oxo-2-quinoxaline carboxylic acid rimantadine salt
J. 6,7-dibromo-3,4-dihydro-3-oxo-2-quinoxaline carboxylic acid spiroamine salt
K. 6,7-dibromo-3,4-dihydro-3-oxo-2-quinoxaline carboxylic acid cyclooctylamine salt
L. 6,7-difluoro-3,4-dihydro-3-oxo-2-quinoxaline carboxylic acid 1-adamantylamine salt
M. 6,7-dibromo-3,4-dihydro-3-oxo-2-quinoxaline carboxylic acid norbornylamine salt In Table 1, column 1 gives the letter designation of salt; column 2, the dose in mg/kg; column 3, the route of administration; column 4, the survival index (S.I.); column 5, the mean day of death; and column 6, number of survivors over total number of mice. Statistically significant data are indicated by an asterisk.

TABLE 1

| Compound Letter Designation | Dose mg/kg | Route of Administration | Survival Index (S.I.) | Mean Day of Death | Survivors Total Number |
|---|---|---|---|---|---|
| B | 40 | IP | 5.0772* | 9.5 | 16/18 |
| B | 80 | " | 5.0463* | 9.7 | 15/18 |
| C | 40 | " | 4.3056* | 9.5 | 13/18 |
| C | 80 | " | 5.1080* | 9.0 | 17/18 |
| A | 80 | " | 4.9846* | 9.0 | 16/17 |
| Control | 0 | " | 2.5926 | 8.7 | 5/18 |
| " | 0 | " | 3.2716 | 8.6 | 9/18 |
| A | 80 | " | 5.5972* | 9.0 | 17/18 |
| K | 20 | " | 3.1204 | 8.2 | 4/18 |
| K | 40 | " | 3.0231 | 8.3 | 3/18 |
| K | 80 | " | 4.4722* | 8.5 | 10/18 |
| Control | 0 | " | 2.4522 | 7.6 | 5/18 |
| " | 0 | " | 3.2176 | 8.2 | 5/18 |
| M | 20 | " | 3.2932 | 8.1 | 4/18 |
| M | 40 | " | 4.0864 | 8.3 | 6/18 |
| M | 80 | " | 5.3765* | 8.8 | 8/18 |
| A | 80 | " | 7.3472* | 9.0 | 17/18 |
| Control | 0 | " | 2.1250 | 8.1 | 1/18 |
| " | 0 | " | 3.1265 | 8.4 | 2/18 |
| H | 80 | " | 6.8781* | 8.3 | 15/18 |
| F | 80 | " | 6.0710* | 9.4 | 9/18 |
| A | 80 | " | 6.2886* | 8.3 | 12/18 |
| E | 80 | " | 6.5972* | 9.3 | 10/17 |
| Control | 0 | " | 2.9306 | 8.7 | 0/18 |
| " | 0 | " | 3.1914 | 8.3 | 3/18 |
| A | 80 | " | 7.0772* | 9.3 | 9/18 |
| L | 40 | " | 2.9288 | 7.6 | 0/18 |
| L | 80 | " | 3.1991 | 7.6 | 1/18 |
| J | 40 | " | 5.9830* | 8.5 | 5/18 |
| J | 80 | " | 6.1559* | 8.7 | 3/18 |
| Control | 0 | " | 1.7037 | 7.1 | 0/18 |
| " | 0 | " | 2.3025 | 7.4 | 0/18 |
| G | 20 | " | 5.8333* | 8.9 | 8/18 |
| G | 40 | " | 7.1096* | 8.8 | 14/18 |
| G | 80 | " | 7.5417* | 9.7 | 14/17 |
| G | 120 | " | 7.6157* | 19.0 | 14/17 |
| Control | 0 | " | 2.4120 | 8.3 | 0/18 |
| " | 0 | " | 2.6559 | 8.2 | 2/18 |
| A | 80 | " | 7.6389* | 9.7 | 15/18 |
| C | 80 | " | 6.2562* | 9.2 | 5/18 |
| G | 80 | " | 7.7778* | 10.0 | 15/18 |
| Control | 0 | " | 2.6852 | 7.8 | 0/18 |
| " | 0 | " | 2.3117 | 7.7 | 0/18 |
| C | 80 | oral | 4.7635* | 7.9 | 9/18 |
| G | 80 | " | 6.5095* | 9.3 | 12/18 |
| A | 80 | " | 5.6762* | 9.2 | 6/18 |
| B | 80 | " | 5.1762* | 8.6 | 7/18 |
| Control | 0 | " | 3.1762 | 8.3 | 2/18 |
| " | 0 | " | 3.3770 | 7.5 | 1/17 |

Quinoxaline-2-carboxylic acid salts of selected hindered amines have been shown by the data in the above table, to have in vivo activity against influenza virus, A strain. The salts of this invention show similar activity against the Maryland B strain of influenza virus in vivo. For example the 6,7-dibromo-3,4-dihydro-3-oxo-2-quinoxaline carboxylic acid salt of 1-aminoadamantane is active I.P. at 80 mg/kg.

For in vitro use, the compounds can be formulated by dissolving them in water or a lower alkanol, for example, ethanol or methanol. The antiviral composition containing the quinoxaline carboxylic acid-amine salt as the active ingredient is, therefore, applied to the virus habitat in vitro, such habitats including walls of hospital rooms, laboratory benches, laboratory glassware, and the like. The salts can also be added to tissue culture to suppress viral growth therein. For in vivo use, the compounds can be administered either parenterally or orally. For parenteral administration, as by the intraperitoneal route employed in the above experimental work, the compound is administered as a suspension. Oral administration is, of course, preferred. For such use, a quinoxaline salt is mixed with one or more standard pharmaceutically-acceptable extending media such as starch, sucrose, lactose, calcium carbonate etc. and the mixture loaded into empty telescoping gelatin capsules, such that each capsule contains an amount of the salt effective to suppress the growth of influenza virus, either prospective or present. In other words, the salts can be used prophylactically or as curative agents. Alternatively, the drug can be mixed with various excipients including starch, lubricating agents, wetting agents, etc., such as stearic acid, magnesium sterate and the like, and the mixture pressed into tablets, each tablet containing an amount of the drug effective to abort or cure an attack of influenza. Such tablets can be scored so as to provide half or quarter dosages where the drug is to be administered to children. The compounds can also be administered in aqueous suspension.

The dosage rate for mammals is from 1 to 50 mg/kg/day. The dosage range in humans is from 100–1000 mg from 1–4 times a day. Conveniently, a dose of 400 mg of an example, the 1-adamantylamine salt of 6,7-dibromo-3,4-dihydro-3-oxo-2-quinoxaline carboxylic acid, one to four times a day can be administered orally to persons suffering from an influenza infection or who have been exposed to an influenza virus, particularly of the A or B strain.

The salts of this invention are administered to mammals susceptible to infection with influenza virus including horses, mice, pigs and humans. Among humans, the compounds are administered prophylactically particularly to the elderly, to young children, to nurses and doctors, and other hospital or public health personnel, when there is evidence of an imminent "flu" epidemic. The compounds can also be given to anyone having a known exposure to a person with "flu". It is a particular advantage of the therapeutic processes of this invention that the salts may be administered either prophylactically or therapeutically to patients without a preliminary determination that the virus to be combated is influenza virus A strain or B strain, since the salts are effective against both strains.

We claim:

1. A salt of the formula

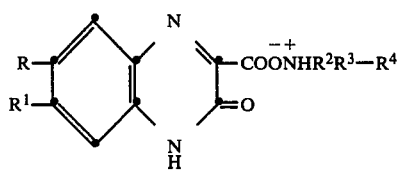

wherein R and $R^1$ are the same or different halogens of the group consisting of F, Cl, Br and I; $R^2$ is H, $CH_3$, or $C_2H_5$, $R^3$ when taken singly is H, $CH_3$, $C_2H_5$, $C_2H_4OH$, $CH_2C_6H_5$ or $CH_2COOC_2H_5$; $R^4$, when taken singly is a hindered hydrocarbyl radical of the group consisting of cyclooctyl, norbornyl, Ad and $CHR^2Ad$; wherein Ad is a 1-adamantyl radical of the formula

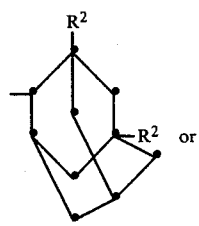

a 2-adamantyl radical of the formula

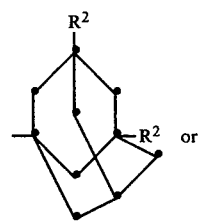

a 3-(4-homoiso)twistane radical of the formula

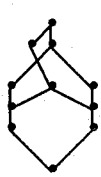

or a tricycloundecane radical of the formula

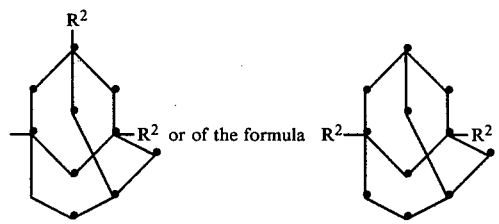

wherein $R^2$ has the same meaning as hereinabove. and $R^4$ when taken together with the nitrogen atom to which they are attached, form an adamantylspiropyrrolidine of the formula

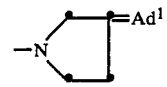

wherein $Ad^1$ is an adamantyl diradical of the formula

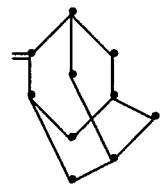

2. A salt according to claim 1 in which R and $R^1$ are Cl or Br.

3. A salt according to claim 1, of the formula

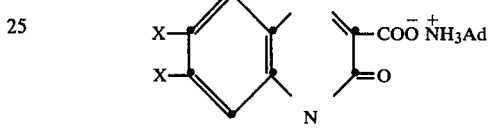

in which X is Cl or Br and Ad is

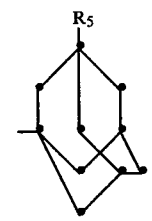

wherein $R^5$ is H or $CH_3$.

4. A salt according to claim 3, said salt being the 1-adamantylamine salt of 6,7-dibromo-3,4-dihydro-3-oxo-2-quinoxaline carboxylic acid.

5. A salt according to claim 3, said salt being the 1-adamantylamine salt of 6,7-dichloro-3,4-dihydro-3-oxo-2-quinoxaline carboxylic acid.

6. A salt according to claim 3, said salt being the 3-methyl-1-adamantylamine salt of 6,7-dibromo-3,4-dihydro-3-oxo-2-quinoxaline carboxylic acid.

7. A salt according to claim 3, said salt being the 3-methyl-1-adamantylamine salt of 6,7-dichloro-3,4-dihydro-3-oxo-2-quinoxaline carboxylic acid.

8. A pharmaceutical preparation in dosage unit form adapted for administration to suppress the growth of influenza A and/or B virus in vivo, consisting essentially of, per dosage unit, a pharmaceutical diluent and an antiviral amount within the range 75–250 mg. of a salt according to claim 1.

9. A 1-methylspiropyrrolidine-3,2'-tricyclo[3.3.1.1$^{3,7}$]decane salt of a 6,7-dihalo-3,4-dihydro-2-oxo-3-quinoxaline carboxylic acid of the formula

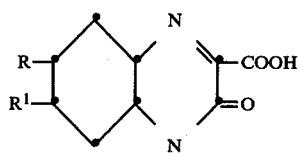

wherein R and $R^1$ are the same or different halogens of the group consisting of F, Cl, Br or I.

10. A salt according to claim 9, said salt being the 1-methyl spiropyrrolidine-3,2'-tricyclo[3.3.1.1$^{3,7}$]decane salt of 6,7-dichloro-3,4-dihydro-2-oxo-3-quinoxaline carboxylic acid.

11. A pharmaceutical method according to claim 8 in which the active antiviral agent is the 1-adamantylamine salt of 6,7-dibromo-3,4-dihydro-3-oxo-2-quinoxaline carboxylic acid.

12. A method for suppressing an influenza viral infection in mammals which comprises administering to a mammal susceptible to infection by influenza virus a dose of a pharmaceutical composition containing a salt according to claim 1 effective to suppress the growth of influenza virus.

13. A method according to claim 12 in which the amount of salt administered is to a human mammal is in the range 100-1000 mg.

14. A pharmaceutical preparation according to claim 8 which the active antiviral agent employed is a salt of the formula

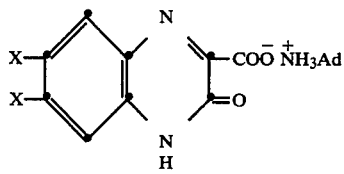

in which X is Cl or Br and Ad is

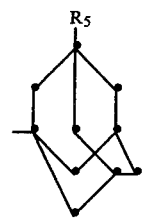

wherein $R^5$ is H or $CH_3$.

15. A pharmaceutical preparation according to claim 8 in which the active antiviral agent is the 1-adamantylamine salt of 6,7-dichloro-3,4-dihydro-3-oxo-2-quinoxaline carboxylic acid.

16. A method according to claim 12 in which a salt of the formula

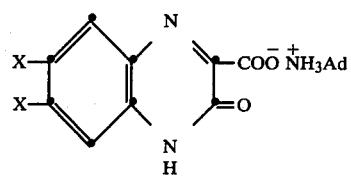

in which X is Cl or Br and Ad is

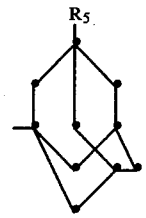

wherein $R^5$ is H or $CH_3$, is administered.

17. A method according to claim 12 in which the 1-adamantylamine salt of 6,7-dibromo-3,4-dihydro-3-oxo-2-quinoxaline carboxylic acid is administered.

18. A method according to claim 12 in which the 1-adamantylamine salt of 6,7-dichloro-3,4-dihydro-3-oxo-2-quinoxaline carboxylic acid is administered.

* * * * *

UNITED STATES PATENT AND TRADEMARK OFFICE
CERTIFICATE OF CORRECTION

PATENT NO. : 4,252,954

DATED : February 24, 1981

INVENTOR(S) : Riaz F. Abdulla et al.

It is certified that error appears in the above-identified patent and that said Letters Patent are hereby corrected as shown below:

Column 17, line 65, delete the word "and" at the end of the line.

Column 17, delete all of lines 66-68.

Column 18, delete all of lines 1-18.

Signed and Sealed this

Nineteenth Day of May 1981

[SEAL]

Attest:

RENE D. TEGTMEYER

Attesting Officer    Acting Commissioner of Patents and Trademarks